United States Patent [19]

Berkelhammer et al.

[11] 4,239,777
[45] Dec. 16, 1980

[54] (−)-α-CYANO-M-PHENOXYBENZYL(+)-α-ISOPROPYL-4-DIFLUOROMETHOXYPHENYLACETATE

[75] Inventors: Gerald Berkelhammer, Princeton; Venkataraman Kameswaran, Princeton Junction, both of N.J.

[73] Assignee: American Cyanamid Company, Stamford, Conn.

[21] Appl. No.: 98,001

[22] Filed: Nov. 28, 1979

Related U.S. Application Data

[63] Continuation-in-part of Ser. No. 890,586, Mar. 20, 1978, Pat. No. 4,199,595, which is a continuation-in-part of Ser. No. 814,600, Jul. 11, 1977, abandoned, which is a continuation-in-part of Ser. No. 728,818, Oct. 1, 1976, abandoned.

[51] Int. Cl.³ .................... A01N 37/34; C07C 121/75

[52] U.S. Cl. .................... 424/304; 260/465 D; 260/544 D; 562/465

[58] Field of Search .................... 260/465 D; 424/304

[56] References Cited

U.S. PATENT DOCUMENTS 3,996,244  12/1976  Fujimoto et al. ............. 260/332.2 A

FOREIGN PATENT DOCUMENTS 2757066  2/1979  Fed. Rep. of Germany.

Primary Examiner—Dolph H. Torrence
Attorney, Agent, or Firm—H. G. Jackson

[57] ABSTRACT

The invention is the compound (−)-α-cyano-m-phenoxybenzyl(+)-α-isopropyl-4-difluoromethoxyphenylacetate.

4 Claims, No Drawings

(−)-α-CYANO-M-PHENOXYBENZYL(+)-α-ISO-PROPYL-4-DIFLUOROMETHOXYPHENYLACETATE

This is a continuation-in-part application of our Ser. No. 890,568 filed Mar. 20, 1978, U.S. Pat. No. 4,199,595 which was a continuation-in-part of application Ser. No. 814,600 filed July 11, 1977 now abandoned which in turn is a continuation-in-part of now abandoned application Ser. No. 728,818 filed Oct. 1, 1976.

The invention is the compound (−)-α-cyano-m-phenoxybenzyl(+)-α-isopropyl-4-difluoromethoxyphenylacetate of the formula:

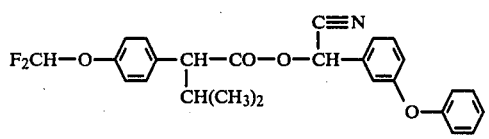

[(+)-acid (−)-alcohol].

Preparation of (−)-α-Cyano-m-phenoxybenzyl (+)-α-Isopropyl-4-difluoromethoxyphenylacetate A mixture of 7.0 g of (+)-α-cyano-m-phenoxybenzyl (+)-α-isopropyl-4-difluoromethoxyphenylacetate in 100 ml of ether was injected onto a silica gel cartridge, previously conditions with hexane/ether (8:1), in a Waters Prep LC/System 500 liquid chromatograph. An ultraviolet detector was used to observe the presence of product ester in the eluant. After recycling the product eluant three times using hexane/ether (8:1) at 250 ml/min., the two diasteromers were detected with retention times of 9.7 and 9.9 minutes. On the next 4 passes, eluant containing the first peak was progressively shaved off and discarded while the second peak eluant was shaved and collected. The collected fractions were combined and concentrated in vacuo to give 2.4 g of colorless viscous oil. The product was assayed by gas-liquid chromatography on a 4 meter column of 3% SP-2401 on 100/120 Supelcoport using a hydrogen/helium (1.5:1) gas mixture at 75 ml/min and flame ionization detection. The injection port temperature was 230° C. and the column temperature was 228° C.

The products peaks eluted at 31.4 and 35.4 min. with the latter, which includes the desired product ester, representing 99.3% of the total. Chemical purity, when other peaks were accounted for, was 94.7%.

$[\alpha]_D = -6.50°$ (CHCl$_3$, C=1.555 g/100 ml).

NMR (CDCl$_3$) β6.44 (t, J=73–74 Hz, 1 H, OCHF$_2$), β6.38 (s, 1 H, CH—CN), β3.27 [d, J=10 Hz, 1 H, CH—CH(CH$_3$)$_2$], β2.3 (m, 1 H, —CH(CH$_3$)$_2$, β0.95 and β0.70 (pair of doublets, J=7 Hz, 6 H, —CH$_3$).

Further, nomenclature for this compound is (S)-α-cyano-m-phenoxybenzyl (S)-α-isopropyl-4-difluoromethoxyphenylacetate.

EXAMPLE 1

Preparation of α-Isopropyl-4-difluoromethoxyphenylacetic acid

Into an 80° C. magnetically stirred mixture of 10.00 g (0.0515 mol) of α-isopropyl-4-hydroxyphenylacetic acid, 65 ml of dioxane, 19.08 g(18.56 g real, 0.464 mol) of sodium hydroxide, and 30 ml of water is bubbled 46 g (0.532 mol) of chlorodifluoromethane over a period of 4 hours. The reaction mixture is poured into 250 ml of ice water and the resulting mixture is washed with ether, acidified with concentrated hydrochloric acid to pH 3, and then extracted with 200 ml of ether. The ether solution is washed once with 100 ml of water, dried with sodium sulfate, filtered, and then evaporated to give a white paste. A mixture of hexane and methylene chloride is added, and the resulting mixture is filtered to remove the solid which is the starting material. The filtrate is evaporated to give 5.41 g of a clear brown oil. It is estimated that the product was at least 85% pure by nmr.

NMR (CDCl$_3$—d$_5$ pyridine), δ7.43 (d, J=8.2 Hz, 2H), δ7.08 (d, J=8.2 Hz, 2H), δ6.57 (t, J=74.3 Hz, 1H), δ3.63 (s, imp.), δ3.25 (d, J=10 Hz, 1H), δ2.37 (m, 1H), δ1.19 (d, J=6.5 Hz, 3H), δ0.78 (d, J=6.5 Hz, 3H), δ13.82(s, 1H).

EXAMPLE 2

Preparation of α-Isopropyl-4-difluoromethoxyphenylacetyl Chloride.

A solution of α-isopropyl-4-difluoromethoxyphenylacetic acid (4.39 g) and thionyl chloride (3.7 ml) in benzene (20 ml) is refluxed for 4 hours. Evaporation of the solvent and excess thionyl chloride gives the acid chloride which is used as such for esterification. IR band 1800 cm$^{-1}$.

EXAMPLE 3

Preparation of α-Cyano-m-phenoxybenzyl α-Isopropyl-4-difluoromethoxyphenylacetate.

A solution of α-isopropyl-4-difluoromethoxyphenylacetyl chloride (4.82 g) in methylene chloride (10 ml) is added to a methyl chloride solution (10 ml) of α-cyano-m-phenoxybenzyl alcohol (4.05 g) and pyridine (1.5 ml). The mixture is stirred over the weekend and filtered. The filtrate and the washings are evaporated and the residual oil (6.29 g) is purified on a silica column using 1:1 methylenechloride-hexane as eluent. The solvent was evaporated and the residue treated with sodium borohydride and the resulting product purified on a silica gel column to give 2.01 g of product.

NMR (CDCl$_3$), δ0.88 (four doublets, J=6 Hz, 6H, CH$_3$), δ2.30 [m, 1H,

—CH—CH(CH$_3$)$_2$], δ3.24 [d, J=10.1 Hz, 1H, δ6.33 (two singlets, 1H,

δ6.45 (t, J=74 Hz, 1H, CHF$_2$O-), δ7.16 (m, 13H, ArH).

Analysis calculated for C$_{26}$H$_{23}$F$_2$NO$_4$: C, 69.17%; H, 5.13%; F, 8.42%; N, 3.10%. Found: C, 69.41%; H, 5.20%; F, 10.25%; N, 3.70%.

EXAMPLE 4

Resolution of α-Isopropyl-4-difluoromethoxyphenylacetic Acid

A warm solution (60° C.) of (−)-2-phenethylamine (4.96 g) in aqueous ethanol (60% ethanol, 20 ml) is added to a warm solution (60° C.) of the racemic acid (20 g) in aqueous ethanol (60% ethanol, 50 ml) with magnetic stirring. As the solution is allowed to cool slowly to room temperature, the salt precipitates out as white crystalline solid. The mixture is allowed to stand overnight and the solids are collected by filtration, washed with aqueous ethanol (10 ml) and dried (9.5 g): m.p. 184°–188° C. The resolved acid obtained from the above salt is found to have a rotation $[\alpha]_D^{R.T} = +37.1°$ (CHCl$_3$, C=1.439 g/100 ml). Two more crystallizations of the above salt from aqueous ethanol (60% ethanol) give white needles, m.p. 185°–187° C., from which the resolved acid is obtained with $[\alpha]_D^{R.T} = +40.4°$ (CHCl$_3$, C=1.353 g/100 ml).

EXAMPLE 5

Preparation of (+)-α-Isopropyl-4-difluoromethoxyphenyl-acetyl Chloride.

The subject compound can be prepared by treating a solution of (+)-α-isopropyl-4-difluoromethoxyphenylacetic acid with thionyl chloride in benzene, as described in Example 2 above.

EXAMPLE 6

Preparation of (±)-α-Cyano-m-phenoxybenzyl(+)-α-Isopropyl-4-difluoromethoxyphenylacetate.

The subject compound can be prepared by treating a solution of (+)-α-isopropyl-4-difluoromethoxyphenylacetyl chloride in methylene chloride with α-cyano-m-phenoxybenzyl alcohol in methylene chloride and pyridine, as described in Example 3 above.

The (±)-α-cyano-m-phenoxybenzyl (+)-α-isopropyl-4-difluoromethoxyphenylacetate is a colorless viscous oil. $N_D^{23} = 1.5432$.

NMR (CDCl$_2$) δ6.8 to 7.5 (m, 13H, ArH), δ6.43 (t, J=74 Hz, 1H, OCHF$_2$), δ6.30 and 6.23 (2S, 1H, CH—CN), δ3.27 [d, J=10 Hz, 1H, C$\underline{H}$-CH(CH$_3$)$_2$].

Determination of the topical LC$_{50}$ of (−)-α-Cyano-m-phenoxybenzyl (+)-α-isopropyl-4-difluoromethoxyphenylacetate.

Procedure

Third instar tobacco budworm (*Heliothis virescens*) and southern armyworm (*Spodoptera eridania*) larvae were treated topically with 1.0 ug (10 vernier units) of reagent grade acetone containing the desired rate of the test compound. Treatments were made with a ½ cc tuberculin syringe fitted with #26 gauge hypodermic needle and driven by the spindle of a micrometer. The larvae were then placed into petri dishes containing moistened filter paper and allowed to feed on untreated cotton leaves (tobacco budworm) or Sieva lima bean leaves (southern armyworm). The dishes were placed in a holding room in which the temperature was 26.7° C. Mortality data were taken at 72 hrs. posttreatment. The data were analyzed using probit analysis, and are given below:

| Insect | LC$_{50}$ (μg larvae) |
|---|---|
| Third instar tobacco budworm larvae | 0.0005 |
| Southern armyworm larvae | 0.0010 |

EXAMPLE 7

Evaluation of the insecticidal activity of the compound of the invention.

Methods

1. Malaria Mosquito (*Anopheles Quadrimaculatus*), eggs and 1st instar.

Formulations

The compound is dissolved in 50:50 acetone water to yield solutions of 300, 100, 10, 1 and 0.1 ppm concentration, respectively.

Test procedure

One ml each of the above solutions is pipetted with stirring into a 400 ml beaker containing 250 ml of deionized water, to yield the test concentrations of 1.2, 0.4, 0.04, 0.004 and 0.0004 ppm, respectively. A wax paper ring about 1 cm wide and 6.5 cm in diameter to fit inside the beaker is floated on the surface of the test solution to keep the eggs from floating up the meniscus curve and drying out on the side of the beaker. A spoon made out of screen is used to scoop up and transfer about 100 eggs (6–30 hours old) into the test beaker. The beakers are held for 2 days at 27° C. and then kill of eggs and newly hatched larvae is determined. The data are given in Table I below.

2. Tobacco budworm (*Heliothis virescens*), egg.

Formulations

The compound to be tested is dissolved in 50:50 acetone: water to yield solutions of 300, 100 and 10 ppm concentration, respectively.

Plant preparation

Cotton plants with the first true leaf expanded about 6–7 cm in length are selected for the test.

Insect preparation

Eggs are collected on cheesecloth used as the lid for the moth oviposition chamber in the rearing colony. This cloth is cut into 10–20 mm squares containing about 50–100 budworm eggs laid within the past day. Thus, eggs are 6–30 hours old when used in the test.

Test procedure

The cotton plant is dipped in the test formulation and agitated for 3 seconds. A square of cheesecloth with eggs is also dipped in the test formulation, placed on the treated leaf and the combination placed in a hood to air dry. When dry, the leaf and egg cloth are removed from the plant, and placed in an "8-ounce Dixie cup #2168ST" (240 ml, 6 cm high, top diameter 9.5 cm, botton diameter 8 cm), to which a 5 cm length of damp cotton dental wick had been previously added. A clear plastic lid (Dixie #3068G) is placed on the cup, and the cups are held at 27° C. until the eggs hatch, which occurs in about 2 days. The cups are then examined for kill of eggs. The results are recorded in Table I below.

3. Tobacco budworm (*Heliothis virescens*), 1st instar.

Formulations

The compound to be tested is dissolved in 50:50 acetone: water to yield solutions of 300, 100 and 10 ppm concentration, respectively.

Plant preparation

Cotton plants with the first true leaf expanded about 6–7 cm in length are selected for the list.

Insect preparation

Cheesecloth on which moths have oviposited is daily cut into 10–20 mm squares containing 50–100 eggs each. These squares are held at 21° C. for two days and at 24° C. for another day in order to coordinate batch with testing times. Thus, the worms are 0–2 hours old at the time of use.

Test procedure

The cotton plant is dipped in the test formulation, agitated for 3 seconds, and placed in a hood to dry. When dry, the leaf is removed from the plant and placed in an "8-ounce Dixie cup #2168 ST" (240 ml, 6 cm high, top diameter 9.5 cm, bottom diameter 8 cm) to which a 5 cm length of damp cotton dental wick had been previously added. A square of cheesecloth with newly hatched budworm larvae on it is placed on the treated leaf, a clear plastic lid (Dixie #3068 G) is put on the cup, and the cups are held at 27° C. for two days. After two days mortality counts are made. Observation of the amount of feeding is also recorded. Where there is only trace to light feeding, the cup is held an extra day and results recorded at that time.

4. Phosphate resitant 2-spotted spider mite (*Tetranychus urticae*), adults, eggs, nymphs.

Formulations

The compound to be tested is dissolved in 50:50 acetone: water to yield solutions of 300, 100 and 10 ppm concentration, respectively.

Plant and Mite preparation

Sieva lima bean plants with primary leaves 7–8 cm long are selected and cut back to one plant per pot. A small piece is cut off of a leaf taken from the main mite colony and placed on each leaf of the test plants. This is done about 1–3 hours before use to allow the mites to move over to the test plant and lay eggs before treatment. The size of the piece cut is varied to try to obtain about 100 mites per leaf.

Test procedure

The piece of leaf used to transfer mites is removed and discarded. The mite-infested plant is dipped in the test formulation for 3 seconds with agitation, and the plant set in a hood to dry.

The plants are held for 2 days at 27° C. for the first observation, and the second leaf is kept on the plant for another 4 days for the final observation.

After 2 days one leaf is removed and examined under a 10× microscope to determine the mortality of adult mites. The second leaf is examined similarly 7 days after treatment to observe the kill of eggs and of newly hatched larvae giving a measure of ovicidal and residual action, respectively. The data obtained are recorded in Table I below.

5. Southern armyworm (*Spodoptera eridania*), 3rd instar.

Formulations

The compound to be tested is dissolved in 2:1 acetone: water to yield solutions of 1000, 100 and 10 ppm concentration, respectively.

Plant preparations

Sieva lima bean plants are selected with primary leaves 7–8 cm long and cut back to one plant per pot.

Insect preparation

The bottom of a 100×10 mm petri dish is lines with a damp filter paper and ten 3rd instar larvae, each about 10 mm long, are added.

Test procedure

The bean plant is dipped in the test solution, agitated for 3 seconds and placed in a hood to dry. When dry, one leaf is removed from the plant and placed in the petri with the caterpilars. The dish is held at 27° C. The plant with the remaining leaf is held in the greenhouse under high intensity lights.

Mortality counts are made after two days. If any reduction in feeding is noted, the dish is held for an additional day and reobserved. Mortality counts and reduced feeding are again determined, and the bean plants treated with compounds considered active are retained in the greenhouse exposed to high intensity lights for a 7-day residual activity test. One week after the original treatment, a leaf is removed from the plant and assayed again by the above procedure. The results yield a measure of the residual activity of the compound under test.

6. Bean aphid (*Aphis fabae*), mixed stages.

Test formulations

The compound to be tested in dissolved in 50:50 acetone: water to yield solutions of 1000, 100, 10, 1 and 0.1 ppm concentrations, respectively.

Plant and insect preparation 5 cm pots each containing a nasturtium plant about 5 cm tall are infested with 100 to 400 aphids 2–4 days before the test.

Test procedure

The pot of aphids is sprayed for 2 revolutions of a 4 rpm turntable in the hood, using a #154 DeVilbiss atomizer at 0.15 kg/cm$^2$ pressure. The spray tip is held about 15 cm from the plant and the spray directed so as to give complete coverage of the aphid and the plants. The sprayed plants are laid on their sides on white enamel trays measuring 24×34 cm. Trays of sprayed pots are held at 27° C. for 1 day, and mortality counts are then made. The results are recorded in Table II below.

7. Southern corn rootworm (*Diabrotica undecimpunctata howardi*), larvae.

Test solutions

The compound under test is dissolved in acetone at the appropriate concentrations, aliquots of which when added to 25 ml of moist potting soil correspond to the kg/ha rates given in Table II.

Test procedure

Into each 30 ml wide-mouth screw top glass jar place about 1 ml of finely divided talc. Pipette onto the talc 1.25 ml of the appropriate solution and evaporate the acetone under a mild air stream. Work up the treated talc into a dust, add 25 ml of moist potting soil (about 25% of moisture holding capacity) and 1 ml of millet seed to serve as food for the insects. Cap the jar and thoroughly mix on a vortex mixer for about 36 seconds. After mixing, place 10 southern corn rootworm larvae (about 6–8 days old) in the jar and cap loosely. The jars are held at 27° C. for 6 days, the soil is then dumped out and searched for worms. Missing worms are presumed to have died, since dead worms decompose very rapidly. The data obtained are recorded in Table II below.

8. Tarnished plant but (*Lygus lineolaris*), adult.

Formulation

The compound to be tested is dissolved in 50:50 acetone: water at 100 and 10 ppm concentration.

Test procedure

Insects are aspirated out of the rearing colony and placed ten to a container. The container is an "8-ounce Dixie cup No. 2168 ST" (240 ml, 6 cm high, top diameter 9.5 cm, bottom diameter 8 cm) to which a 5 cm damp cotton dental wick had been previously added.

Sieve lima bean plants, with leaves about 5 cm long are dipped in the test formulation, agitated for 3 seconds, and placed in a hood to dry. When dry, a leaf is removed and placed in the cup with the insects, and then the cup is covered with a clear plastic lid (Dixie #3068G). The cup is held at 27° C. for two days.

Mortality counts are made after two days and recorded in Table II below.

9. Western potato leafhopper (*Empoasca abrupta*), adults.

Formulations

The compound under test is dissolved in 50:50 acetone: water to yield solutions 100, 10 and 1 ppm, respectively.

Plant preparations

Sieva lima bean plants are selected with primary leaves about 5 cm long.

Insect preparation

The bottom of a 100×10 mm petri dish is lined with a damp filter paper.

Test procedure

The bean plant is dipped in the test solution, agitated for 3 seconds and placed in a hood to dry. One leaf is removed and placed in the petri dish. The dish is taken to the colony of insects, 5-10 leafhoppers are tapped into the dish and it is then rapidly covered. The dish is held at 27° C. for two days, mortality counts are then made and recorded in Table II below.

10. Tobacco budworm (*Heliothis virescens*), 3rd instar.

Formulations

The compound to be tested is dissolved in 2:1 acetone: water to yield solutions of 1000, 100 and 10 ppm concentration, respectively.

Test procedure

Cotton cotyledons are dipped in the solutions and dried in a hood. When dry, each cotyledon is cut into quarters, and ten sections are placed individually in 30 ml plastic medicine cups containing a 5-7 mm long piece of damp cotton dental wick. One 3rd instar budworm larvae is added to each cup and a cardboard lid placed on the cup. The cups are held at 27° C. for 3 days. Mortality counts and observations of reduced feeding are then made.

11. Cabbage looper (*Trichoplusia ni*), 3rd instar.

Formulations

The compounds to be tested are dissolved in 2:1 acetone: water to yield solutions of 1000, 100 and 10 ppm concentration, respectively.

Plant preparation

Cotton plants with the first time leaf expanded about 7-8 cm in length are selected for the test.

Insect preparation

The bottom of a 100×10 mm petri dish is lined with a damp filter paper and ten 3rd instar larvae are added.

Test procedure

The cotton plant is dipped in the test solution, agitated for 3 seconds and placed in a hood to dry. When dry, the leaf is placed on the petri dish with the insects. The dish is held at 27° C. for one or two days, and then mortality counts and observations of reduced feeding are made.

Malaria mosquito (*Anopheles Quadrimaculatus*), adult.

Formulations

The compound under test is dissolved in acetone to yield solutions of 10 and 1 ppm concentration.

Test procedure

Acetone solutions are poured into wide-mouth 60 ml jars, each containing a microscope slide. The slides are removed from the test solution with clean forceps and laid horizontally to dry on the mouth of a wide-mouth 120 ml bottle. Ten 4- to 5-day old adult mosquitoes of mixed sexes are aspirated from a carton of adults and placed in the bottle with the treated microscope slide. A piece of cheesecloth held on by an elastic band serves as a lid and a wad of cotton coated in 10% honey solution is placed on the cheesecloth as a food source. The jars of mosquitoes are held at 27° C. for one day. Mortality counts are then made and data recorded in Table II below.

TABLE I

| Percent[1] mortality counts are given at the parts per million (ppm) concentrations shown | | | | | | | | | | | | | | | | | |
|---|---|---|---|---|---|---|---|---|---|---|---|---|---|---|---|---|---|
| Mosquito | | | | | | | Tobacco - Budworm | | | | | | | | | | |
| Eggs ppm | | 1st instar larvae ppm | | | | | Eggs ppm | | | | | | 1st instar larvae ppm | | | | |
| 1.2 | 0.4 | 1.2 | 0.4 | 0.04 | 0.004 | 0.0004 | 300 | 100 | 10 | 1 | 0.1 | 300 | 100 | 10 | 1 | 0.1 |
| — | | 100 | 100 | 100 | 100 | 85-95 | 100 | 100 | 100 | 55-65 | 0 | 100 | 100 | 100 | 0-25 | 0 |

| Phosphate Restant Unites ppm | | | Southern Army-Worm, 3rd instar ppm | | | |
|---|---|---|---|---|---|---|
| 300 | 100 | 10 | 1000 | 100 | 0 | 1 |
| 100 | 100 | 0 | 100 | 100 | 100 | 0 |

[1] = A range is shown when more than ten insects are used for the test and the mortality count is less than 100%

TABLE II

| Percent[1] mortality counts are given at the parts per million (ppm) concentrations shown, unless otherwise indicated. | | | | | | | | | | | | | | | | | | | | | | |
|---|---|---|---|---|---|---|---|---|---|---|---|---|---|---|---|---|---|---|---|---|---|---|
| Bean Aphids ppm | | | | Southern Corn Rootworm kg/ha | | | Lygus ppm | | Western potato Leaf hopper ppm | | | Tobacco Bud-Worm, 3rd instar ppm | | | | Cabbage Looper, 3rd instar ppm | | | | Mosquito Adult ppm | |
| 1000 | 100 | 10 | 1 | 0.1 | 56 | 11.2 | 1.12 | 100 | 10 | 100 | 10 | 1 R* | 1000 | 100 | 10 | 1 | 1000 | 100 | 10 | 1 | 10 | 1 |
| 100 | 100 | 100 | 100 | 85-95 | 100 | 0 | | 100 | 0 | 100 | 60 | 0 | 1000 | 100 | 60 | 20 | 100 | 100 | 100 | 20 | 100 | 0 |

[1] = A range is shown when more than ten insects are used for the test and the mortality count is less than 100%.
* = R = Repellent.

We claim:

1. The compound (−)-α-cyano-m-phenoxybenzyl-(+)-α-isopropyl-4-difluoromethoxyphenylacetate.

2. A method for controlling insects and acarina comprising contacting the insects and acarina, their habitat, breeding grounds or feed, with an insecticidally or acaricidally effective amount of (−)-α-cyano-m-phenoxybenzyl(+)-α-isopropyl-4-difluoromethoxyphenylacetate.

3. An insecticidal composition comprising (−)-α-cyano-m-phenoxybenzyl(+)-α-isopropyl-4-difluoromethoxyphenylacetate, an emulsifying agent, a surfactant and a solvent.

4. A method for the preparation of the compound (−)-α-cyano-m-phenoxybenzyl (+)-α-isopropyl-4-difluorophenylacetate comprising: reacting (+)-α-isopropyl-4-difluoromethoxyphenylacetyl chloride with α-cyano-m-phenoxybenzyl alcohol in the presence of pyridine and isolating from the thus-obtained mixture of (+)-α-cyano-m-phenoxybenzyl (+)-α-isopropyl-4-difluoromethoxyphenylacetate said (−)-α-cyano-m-phenoxybenzyl (+)-α-isopropyl-4-difluoromethoxyphenylacetate.

* * * * *

UNITED STATES PATENT AND TRADEMARK OFFICE
CERTIFICATE OF CORRECTION

PATENT NO. : 4,239,777              Page 1 of 2
DATED     : December 16, 1980
INVENTOR(S) : Gerald Berkelhammer et al.

It is certified that error appears in the above—identified patent and that said Letters Patent is hereby corrected as shown below:

Column 1, line 27: change "(+)-α-cyano-m-...." to "(±)-α-cyano-m....".

Column 1, line 30: change "conditions" to "conditioned".

Column 1, lines 51 to 55: All β should be changed to δ.

Column 1, line 55; change "CH-CH(C$\underline{H}_3$)$_2$" to "C$\underline{H}$-CH(CH$_3$)$_2$".

Column 2, line 35: change "methyl chloride" to "methylene chloride".

Column 2, lines 45 to 51: change to "δ2.30 [m,1H,-$\overset{|}{C}$H-C$\underline{H}$(CH$_3$)$_2$], δ3.24 [d,J=10.1Hz,1H,-C$\underline{H}$-CH(CH$_3$)$_2$],".

Column 3, line 51: change "a 1/2 cc tuberculin" to "a 1/4 cc tuberculin".

UNITED STATES PATENT AND TRADEMARK OFFICE
CERTIFICATE OF CORRECTION

PATENT NO. : 4,239,777  
DATED : December 16, 1980  
INVENTOR(S) : Gerald Berkelhammer et al.

Page 2 of 2

It is certified that error appears in the above—identified patent and that said Letters Patent is hereby corrected as shown below:

Column 6, line 14: change "to be tested in dissolved" to "to be tested is dissolved".

Table I, under the column Southern Armyworm, 3rd instar ppm: change "1000  100  0  1" to "1000  100  10  1".

Column 10, line 7: change "(+)-α-cyano-$\underline{m}$-phenoxy..." to "($\underline{+}$)-α-cyano-$\underline{m}$-phenoxy...".

Signed and Sealed this

Nineteenth Day of May 1981

[SEAL]

Attest:

RENE D. TEGTMEYER

Attesting Officer

Acting Commissioner of Patents and Trademarks